(12) United States Patent
Singh et al.

(10) Patent No.: US 6,635,621 B1
(45) Date of Patent: Oct. 21, 2003

(54) CYSTEINE PROTEASE INHIBITORS

(75) Inventors: Rajeshwar Singh, Edmonton (CA); Nian Zhou, Woodridge, IL (US); Andhe V. N. Reddy, Edmonton (CA); George Thomas, Edmonton (CA); Qizhu Ding, Edmonton (CA); Jadwiga Kaleta, Edmonton (CA); Ronald George Micetich, Edmonton (CA); Mark Whittaker, Abingdon (GB)

(73) Assignee: Naeja Pharmaceutical Inc., Edmonton (CA)

( * ) Notice: Subject to any disclaimer, the term of this patent is extended or adjusted under 35 U.S.C. 154(b) by 0 days.

(21) Appl. No.: 10/048,396
(22) PCT Filed: Jul. 21, 2000
(86) PCT No.: PCT/GB00/02830
§ 371 (c)(1),
(2), (4) Date: Jan. 30, 2002
(87) PCT Pub. No.: WO01/09169
PCT Pub. Date: Feb. 8, 2001

(30) Foreign Application Priority Data

Jul. 31, 1999 (GB) .............................. 9917909

(51) Int. Cl.$^7$ ........................ C07D 295/12; A61K 38/05
(52) U.S. Cl. ................... 514/19; 544/168; 544/400; 546/233; 548/557; 560/32; 560/159; 564/153
(58) Field of Search ................... 560/159, 32; 564/153; 544/168, 400; 546/233; 548/557; 514/19

(56) References Cited

U.S. PATENT DOCUMENTS 3,216,992 A * 11/1965 Bodanszky .............. 260/112.5

FOREIGN PATENT DOCUMENTS

WO    WO 96/32408    10/1996
WO    WO 98/12176    3/1998

OTHER PUBLICATIONS

Woolley J Org Chem 28 (8) 2012–5 1963.*
March advanced Organic Chemistry 4$^{th}$ ed. pp. 882–884.*
Kakimoto Chemistry Letters pp. 527–528 1982.*
Doran, John D. et al.: "Deacylation and Reacylation for a series of Acyl Cysteine Proteases Including Acyl Groups Derived From Novel Chromophoric Substrates" Biochemistry (1996) 35(38) 12487–12494.
Baggio Ricky et al.: "From poor substrates to good inhibitors: Design of inhibitors for serine and thiol proteases." Biochemistry, vol. 35, No. 11, 1996, pp. 3351–3353.
Duffy K J et al.: "Design and synthesis of diaminopyrrolidinone inhibitors of human osteoclast cathepsin K" Bioorganic & Mechanic Chemistry Letters, vol. 9, No. 14, Jul. 19, 1999.

* cited by examiner

*Primary Examiner*—Robert Gerstl
(74) *Attorney, Agent, or Firm*—Rothwell, Figg, Ernst & Manbeck P.C.

(57) ABSTRACT

This invention relates to derivatives of alpha-amino acid amides, to pharmaceutical compositions containing such compounds, and to their use in medicine as inhibitors of cysteine proteases, particularly the cathepsins. A compound of formula (I) is described or a pharmaceutically acceptable salt, hydrate or solvate thereof. Pharmaceutically acceptable salts of the compounds of this invention include the sodium, potassium, magnesium, calcium, hydrogen chloride, tartaric acid, succinic acid, fumaric acid and p-toluenesulfonic acid salts.

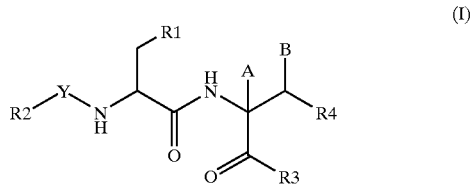

(I)

11 Claims, No Drawings

CYSTEINE PROTEASE INHIBITORS

CROSS REFERENCE TO RELATED APPLICATION

This application is a 35 USC 371 National Phase Entry Application from PCT/GB00/02830, filed Jul. 21, 2000, and designating the U.S.

This invention relates to derivatives of alpha-amino acid amides, to pharmaceutical compositions containing such compounds, and to their use in medicine as inhibitors of cysteine proteases, particularly the cathepsins.

BACKGROUND TO THE INVENTION

The cathepsin family (C1) of lysosomal cysteine (or thiol) proteases is a subset of the papain superfamily (clan CA of cysteine proteases) and includes cathepsin B, H, K, S, L and the recently discovered cathepsins O, O2/K, V, X, Z and W (lymphopain). Related enzymes also regarded as cysteine proteases are the cytoplasmic $Ca^{2+}$ dependent calpains (family C2). Cysteine proteases are classified both functionally and according to the nature of their active site, which has a thiol residue. They differ in substrate specificities and other enzymatic activities, these differences probably arising from evolutionary divergence.

The known cathepains are synthesized on membrane bound ribosomes, transferred to the endoplasmic reticulum, then to the Golgi apparatus and finally to the lysosome and endosomes. They have an important function in regulation of intracellular protein metabolism, mobilisation of tissue proteins and conversion of proenzymes, prohormones and neuropeptides into biologically active molecules. The cathepsins are believed to be involved in a number of diseases.

Cathepsin K can be secreted into the extracellular space and is involved in bone and cartilage remodelling. Cathepsin K is implicated in the pathogenesis of osteoporosis. Cathepsin K inhibitors can prevent osteoporosis in animal models (PNAS.1997. 94:14249–14254). Cathepsin L inhibitors have also been shown to inhibit osteoporosis (Bone, 1997. 20:465–471).

Cathepsin B and other cysteinyl cathepsins have also been shown to be released extracellularly by various tumour cells and are thought to play a role in tumour invasion (Journal of cellular Physiology. 1992. 150:534–544).

The cysteinyl cathepsins have also been shown to play a role in rheumatoid arthritis (Arthritis and Rheumatism 1994. 37:236–247) and neuronal and cardiac ischaemia (European Journal of Neuroscience. 1998. 10.1723–1733).

Cathepsins S and L both play a role in the generation of free MHC class II molecules capable of binding antigenic peptides in the endosomes. These class II/peptide complexes move to the cell membrane and are involved in T lymphocyte activation. Inhibitors of Cathepsin S have been shown to inhibit allergic immune responses (Journal of Clinical Investigation. 1998. 101:2351–2363).

In addition to their role in the above diseases, cysteinyl cathepsins play a major role in the pathogenesis of infectious diseases. For example, cysteinyl cathepsins are used by the protozoal parasites Plasmodium (malaria) and Trypanosoma (Chagas Disease) to invade the human host and cysteinyl cathepsin inhibitors can inhibit experimental disease in both cases (Antimicrobial agents and chemotherapy. 1998. 42:2254–2258; Journal of Experimental Medicine. 1998. 188:725–734). Cysteinyl cathepsins are also virulence factors for several pathogenic bacteria.

A recent review (Annu. Rev. Physiol. 1997. 59:63–88) describes the state of the art of cysteine proteases, including the cathepsins, and their presumed biological functions. Other reviews deal with cathepsin B inhibitors as potential anti-metastatic agents (Exp. Opin. Ther. Patents, 1998, 8: 645–672), and cathepsin K inhibitors as potential treatments for osteoporosis (Exp. Opin. Ther. Patents, 1999, 9: 683–644).

International patent applications WO 96/32408, WO 98/12176, WO 98/12210 and GB 9806287.0 describe, inter alia, classes of cysteine protease inhibitors which may be represented by formula (IA):

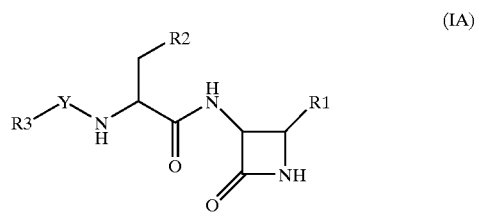

(IA)

wherein Y, $R_1$, $R_2$ and $R_3$ represent the groups found in corresponding positions of the compounds disclosed in those publications. These known compounds are azetidin-2-ones which are monosubstituted at positions 3 and 4.

BRIEF DESCRIPTION OF THE INVENTION

The present invention makes available a new class of cysteine protease inhibitors which differ in structure from those disclosed in WO 96/32408, WO 98/12176, WO 98/12210 and GB 9806287.0 principally in that the azetidin-2-one ring is replaced by a substituted carbonylmethyl moeity, as more fully explained below. These compounds are useful for the treatment of diseases mediated by cysteine protease activity, for example muscular dystrophy, osteoporosis, tumour metastasis, rheumatoid arthritis, neuronal or cardiac ischaemia, allergic immune response, and protozoal or bacterial disease.

DETAILED DESCRIPTION OF THE INVENTION

According to the present invention, there is provided a compound of formula (I)

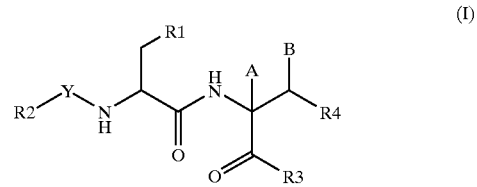

(I)

wherein:
Y represents —C(O)— or —S($O_2$)—;
$R_1$ represents a radical of formula $R_6$—(ALK)$_p$—(Z)$_n$—(ALK)$_q$— wherein Z represents —O— or —S—, ALK represents a divalent $C_1$–$C_3$alkyl or halogen-substituted $C_1$–$C_3$alkyl radical, p and q are independently 0 or 1, n is 0 or 1 when q is 1 and n is 0 when q is 0, and $R_6$ is hydrogen or an optionally substituted $C_1$–$C_6$alkyl, $C_2$–$C_6$alkenyl, $C_2$–$C_6$alkynyl, cycloalkyl, cycloalkenyl, aryl or heterocyclic group; or $R_1$ together with the carbon atom to which it is attached forms a cycloalkyl ring;
$R_2$ represents —$OR_5$ or —$R_5$;
$R_5$ represents a radical of formula $R_7$—(A)$_t$— wherein t is 0 or 1; A represents (i) an optionally substituted divalent $C_1$–$C_6$alkyl, radical which may be interrupted by one or more non-adjacent —O—, —S— or —NH— linkages, or (ii) a divalent $C_2$–$C_6$alkenyl, $C_2$–$C_6$alkynyl, cycloalkyl, cycloalkenyl, aryl or heterocyclic radical, or (iii) a —NH— link; and $R_7$ represents hydrogen or an optionally substituted $C_1$–$C_6$alkyl, $C_2$–$C_6$alkenyl, $C_2$–$C_6$alkynyl, cycloalkyl, cycloalkenyl, aryl or heterocyclic group;

$R_3$ represents (i) an optionally substituted $C_1$–$C_6$alkyl, $C_2$–$C_6$alkenyl, $C_2$–$C_6$alkynyl, cycloalkyl, cycloalkenyl, aryl or heterocyclic group or (ii) $NHR_8$ or $N(R_8)_2$ or (iii) $OR_8$ wherein $R_8$ represents hydrogen or an optionally substituted $C_2$–$C_6$alkyl, $C_2$–$C_6$alkenyl, $C_2$–$C_6$alkynyl, cycloalkyl, cycloalkenyl or aryl;

A and B taken together represent a bond and $R_4$ represents a hydroxy or substituted hydroxy group or an amino or primary or secondary amino group, or A represents hydrogen and B and $R_4$ each independently represents a hydroxy or substituted hydroxy group;

or a pharmaceutically acceptable salt, hydrate or solvate thereof.

Pharmaceutically acceptable salts of the compounds of this invention include the sodium, potassium, magnesium, calcium, hydrogen chloride, tartaric acid, succinic acid, fumaric acid and p-toluenesulfonic acid salts.

As used herein the term ($C_1$–$C_6$)alkyl or lower alkyl means a straight or branched chain alkyl moiety having from 1 to 6 carbon atoms, including for example, methyl, ethyl, propyl, 1-methylethyl, butyl, 1-methylpropyl, 2-methylprop-1-yl, 2-methylprop-2-yl, pentyl, 3-methylbutyl, and hexyl. Similar terms such as "($C_1$–$C_3$)alkyl" are to be interpreted similarly.

As used herein the term $C_2$–$C_6$alkenyl" means a straight or branched chain alkenyl moiety having from 2 to 6 carbon atoms having at least one double bond of either E or Z stereochemistry where applicable. The term includes, for example, vinyl, allyl, 1- and 2-butenyl and 2-methyl-2-propenyl. Similar terms such as "($C_2$–$C_3$)alkenyl" are to be interpreted similarly.

As used herein the term "$C_2$–$C_6$alkynyl" means a straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl. Similar terms such as "($C_2$–$C_3$)alkynyl" are to be interpreted similarly.

As used herein the term cycloalkyl means a saturated alicyclic moiety having from 3–7 carbon atoms and includes, for example, cyclohexyl, cycloheptyl, cyclopentyl, cyclobutyl and cyclopropyl.

As used herein the term "halogen" means fluoro, chloro, bromo or iodo.

As used herein the term "aryl" refers to a mono-, bi- or tri-cyclic, substituted or unsubstituted, carbocyclic aromatic group, and to groups consisting of two covalently linked substituted or unsubstituted monocyclic carbocyclic aromatic groups. Illustrative of such groups are phenyl, biphenyl and napthyl. Examples include $C_6$–$C_{12}$ aryl groups such as phenyl, biphenyl, naphthyl, tetrahydronaphthyl, dihydronaphthyl, and cyclohexyl phenyl.

As used herein the unqualified term heterocyclyl or heterocyclic means a 5–7 membered heterocyclic ring, which may be aromatic or non-aromatic, containing one or more heteroatoms selected from S, N and O, and optionally fused to a benzene or hetero-atom containing ring. The term therefore includes $C_1$–$C_{11}$ heterocyclic groups containing 1–4 heteroatoms selected from nitrogen, sulfur or oxygen. Examples include thienyl, pyridyl, 1,2,3-triazolyl, 1,2,4-triazolyl, 1,2,3,4-tetrazolyl, imidazolyl, quinolinyl, isoquinolinyl, indolyl, pyrimidinyl, benzofuranyl, benzothienyl, morpholinyl, thiomorpholinyl, piperazinyl, piperidinyl, tetrahydroquinolinyl, tetrahydroisoquinolinyl, pyridylphenyl, pyrimidylphenyl, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, and phthalimido groups.

As used herein, the term "primary or secondary amino group" means an amino group carrying one or two substituents respectively, for example selected from amino protecting groups, ($C_1$–$C_6$)alkyl-X—, ($C_2$–$C_6$)alkenyl-X—, ($C_2$–$C_6$)alkenyl-X—, aryl($C_1$–$C_6$)alkyl-X—, aryl($C_2$–$C_6$)alkenyl-X—, aryl($C_2$–$C_6$)alkenyl-X—, heterocyclic($C_1$–$C_6$)alkyl-X—, heterocyclic($C_2$–$C_6$)alkenyl-X—, heterocyclic ($C_2$–$C_6$)alkenyl-X—, wherein —X— represents a bond or a carbonyl —C(O)—, sulphonyl —S($O_2$)—, or oxycarbonyl —O—C(O)— group, and wherein any of the foregoing may be substituted. The term "secondary amino group" also means a substituted or unsubstituted cyclic amino group, such as piperidyl, morpholinyl, thiomorpholinyl, piperazinyl, pyrrolidynyl or azetidinyl.

As used herein, the term "substituted hydroxy group" means a protected hydroxy group or a hydroxy group substituted by, for example, any of the substituents listed in the preceding paragraph as substituents of primary or secondary amino groups except those wherein X is an oxycarbonyl —O—C(O)— group.

As used herein in contexts other than "substituted hydroxy group", the unqualified term "substituted" as applied to a roup or radical means substituted with 1, 2, or 3 ubstituents selected from ($C_1$–$C_3$)alkyl;

phenyl;

hydroxy or mercapto;

($C_1$–$C_3$)alkoxy or ($C_1$–$C_3$)alkylthio;

phenoxy or phenylthio;

halogen;

trifluoromethyl;

nitro;

cyano (—CN);

carboxyl, and amidated, esterified or protected carboxyl;

amino, mono- or di-($C_1$–$C_3$)alkylamino, or protected amino;

($C_1$–$C_3$)alkylcarbonyl- or ($C_1$–$C_3$)alkylcarbonylamino-;

—$CONHR^A$, —$NHR^A$, —$NR^AR^B$, or —$CONR^AR^B$ wherein $R^A$ and $R^B$ are independently ($C_1$–$C_3$)alkyl; and —NH—C(=$NR_9$)$R_{10}$ wherein $R_{10}$ is amino, mono- or di-($C_1$–$C_6$)alkylamino, protected amino, or ($C_1$–$C_3$) alkyl, and $R_9$ is hydrogen, ($C_1$–$C_3$)alkyl, or an N-protecting group.

As used herein the term "protecting group" when used in relation to an amino, hydroxy or carboxylic acid moeity in the compounds of this invention means a group which is used to render the amino, hydroxy or carboxylic acid moeity substantially non reactive, ie to neutralise its amino, hydroxy or carboxylic acid functionality. In this context, protected amino groups include amido and acylamino, protected hydroxy groups include ethers, protected carboxyl groups include esters, and imidazolyl, indolyl or guanidyl groups may be protected as t-butoxycarbonyl derivatives. These are only examples of the many protecting derivatives known in the art, and others will be known to the skilled man. Such protecting groups are of course well known, eg from the art of peptide synthesis, and are discussed in the widely used handbook by T. W. Greene and P. G. M. Wuts, Protective groups in Organic Synthesis, 2nd Edition, Wiley, New York 1991, and elsewhere in the chemical literature.

As mentioned above, the compounds of the invention differ in structure from those of WO 96/32408, WO 98/12176, WO 98/12210 and GB 9806287.0 principally in that the azetidin-2-one ring is replaced by a substituted carbonylmethyl moeity. That substituted carbonylmethyl moeity is the radical (II):

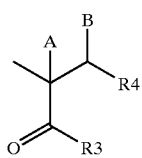

(II)

which may be regarded as notionally derived from the aldehyde radical (III):

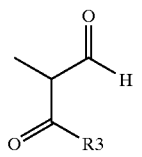

(III)

The substituents $R_1$ and $R_2$ in the compounds of the invention may be any of the groups falling within the above definitions of $R_1$ and $R_2$ which are present in corresponding positions of cysteine protease inhibitors disclosed in WO 96/32408, WO 98/12176, WO 98/12210 and GB 9806287.0. Without prejudice to the generality of the foregoing, in the compounds of the invention:

Y may be, for example, —C(O)—;

$R_1$ may be, for example, a phenyl group which may be substituted by one or more of hydroxy, halogen, methoxy, methyl, isopropyl, tert-butyl and trifluoromethyl; isopropyl, cyclohexyl; 3-pyridinyl; naphthyl; biphenyl; 2-thienyl; 3,4-methylenedioxyphenyl; 3,4-ethylenedioxy-phenyl; benzothienyl; thiazolyl; quinolinyl; isoquinolinyl; tetrahydroquinolinyl; tetrahydronaphthyl; aminonaphthyl; or acetamidonaphthyl. Presently preferred are phenyl, isopropyl, cyclohexyl and 3-pyridinyl.

$R_2$ may be, for example, benzyloxy, 3-phenylpropyloxy, 3-phenylpropyl, 3-phenylprop-1-enyl, 6-N,N-dibenzyloxycarbonylguanidino-hexyl, 6-guanidino-hexyl, methoxy-methyleneoxy-methyl, 2-amino-ethoxy-methyl, 3-(pyridin-3- or 4-yl)-propyl, or 3-(pyridin-3- or 4-yl)-prop-1-enyl.

$R_3$ may be, for example, methyl, ethyl, isopropyl, t-butyl, cyclohexyl, phenyl, 4-methoxyphenyl, 4-fluorophenyl, pyridyl, —NH$_2$, methylamino, dimethylamino, benzylamino, piperidino, morpholino, piperazino, N-methylpiperazino or methoxy, ethoxy, t-butyloxy or phenoxy.

When A and B taken together represent a bond, $R_4$ may be, for example, —NH$_2$, acetylamino, methylamino, dimethylamino, benzylamino, morpholino, piperidino, morpholino, piperazino or N-methylpiperazino, methoxycarbonylmethylamino, (methoxycarbonyl)-phenethylamino, —OH, methoxy, allyloxy, benzyloxy. Alternatively, A may be a hydrogen and B and $R_4$ each independently represents a hydroxy group.

Specific compounds of the invention include those named and characterised in the Examples herein.

2-(2S-2-benzyloxycarbonylamino-2-isopropylmethyl-acetamido)-3-amino-acrylamide 2-(2S-2-benzyloxycarbonylamino-2-cyclohexylmethyl-acetamido)-3-amino-acrylamide 2-(2S-2-benzyloxycarbonylamino-2-benzyl-acetamido)-3-amino-acrylamide 2-[2S-2-(3-phenylpropionoyl)amino-2-benzyl-acetamido]-3-amino-acrylamide 2-(2S-2-benzyloxycarbonylamino-2-isopropylmethyl-acetamido)-3-benzylamino-acrylamide 2-(2S-2-benzyloxycarbonylamino-2-isopropylmethyl-acetamido)-3-(morpholin-4-yl)-acrylamide 2-(2S-2-benzyloxycarbonylamino-2-isopropylmethyl-acetamido)-3-(2-hydroxyethylamino)-acrylamide 2-(2S-2-benzyloxycarbonylamino-2-isopropylmethyl-acetamido)-3-phenylamino-acrylamide 2-(2S-2-benzyloxycarbonylamino-2-isopropylmethyl-acetamido)-3-piperidino-acrylamide 2E)-(2S-2-benzyloxycarbonylamino-2-isopropylmethyl-acetamido)-3-acetamido-acrylamide (2Z)-(2S-2-benzyloxycarbonylamino-2-isopropylmethyl-acetamido)-3-acetamido-acrylamide 2-(2S-2-benzyloxycarbonylamino-2-isopropylmethyl-acetamido)-3,3-dihydroxy-propionamide 2-(2S-2-benzyloxycarbonylamino-2-cyclohexylmethyl-acetamido)-3,3-dihydroxy-propionamide 2-(2S-2-benzyloxycarbonylamino-2-benzyl-acetamido)-3,3-dihydroxy-propionamide 2-[2S-2-(3-phenylpropionoylamino)-2-benzyl-acetamido]-3,3-dihydroxy-propionamide 2-(2S-2-benzyloxycarbonylamino-2-isopropylmethyl-acetamido)-3-hydroxy-acrylamide 2-(2S-2-benzyloxycarbonylamino-2-isopropylmethyl-acetamido)-3-benzylamino-N-benzyl-acrylamide 2-(2S-2-benzyloxycarbonylamino-2-isopropylmethyl-acetamido)-3-(4-methylpiperazino)-acrylamide 2-(2S-2-benzyloxycarbonylamino-2-isopropylmethyl-acetamido)-3-(3-tert-butoxycarbonylamino-pyrrolidino)-acrylamide (2E)-(2S-2-benzyloxycarbonylamino-2-cyclohexymethyl-acetamido)-3-acetamido-acrylamide (2Z)-(2S-2-benzyloxycarbonylamino-2-cyclohexylmethyl-acetamido)-3-acetamido-acrylamide tert-Butyl-2-[2S-(benzyloxycarbonylamino)-2-isopropylmethyl-acetamido]-2-(morpholino-1-methylenyl)-acetate Ethyl-2-[2S-(benzyloxycarbonylamino)-2-isopropylmethyl-acetamido]-2-(4-methylpiperazino-1-methylenyl)-acetate Ethyl-2-[2S-(benzyloxycarbonylamino)-2-phenylmethyl-acetamuido]-2-(morpholino-1-methylenyl)-acetate Ethyl-2-[2S-(benzyloxycarbonylamino)-2-isopropylmethyl-acetamido]-2-(morpholino-1-methylenyl)-acetate Ethyl-2-[2S-(benzyloxycarbonylamino)-2-cyclohexylmethyl-acetamido]-2-(morpholino-1-methylenyl)-acetate Diphenylmethyl-2-[2S-(3-phenylpropionylamino)-2-phenylmethyl-acetamido]-2-(morpholino-1-methylenyl)-acetate 2-[2S-(Benzothiophen-2-carbonylamino)-2-isopropylmethyl-acetamido]-2-(morpholino-1-methylenyl)-4'-methoxyacetophenone.

2-[2S-(Benzyloxycarbonylamino)-2-isopropylmethyl-acetamido]-2-(morpholino-1-methylenyl)-acetophenone.

2-[2S-(Benzyloxycarbonylamino)-2-isopropylmethyl-acetamido]-2-(morpholino-1-methylenyl)-4'-methoxyacetophenone.

2-[2S-(Benzyloxycarbonylamino)-2-isopropylmethyl-acetamido]-2-(morpholino-1-methylenyl)-4'-fluoroacetophenone.

(2E)-(2S-2-benzyloxycarbonylamino-2-phenylmethyl-acetamido)-3-(1-carbomethoxy-2-phenethylamino)-acrylamide (2Z)-(2S-2-benzyloxycarbonylamino-2-phenylmethyl-acetamido)-3-(1-carbomethoxy-2-phenethylamino)-acrylamide (2E)-(2S-2-benzyloxycarbonylamino-2-phenylmethyl-acetamido)-3-(1-carbomethoxy-methylamino)-acrylamide (2E)-(2S-2-benzyloxycarbonylamino-2-phenylmethyl-acetamido)-3-(1-carbomethoxy-methylamino)-acrylamide As stated, the compounds of the invention are inhibitors of cysteine proteases, for example cathepsins B, L, S and/or K. The invention therefore also provides a pharmaceutical composition containing a compound of formula (I) as defined above, and a pharmaceutically acceptable carrier. Also provided is the use of such a compound in the preparation of a composition for inhibiting cysteine protease activity in the body of a mammal suffering a disease mediated by such activity, and a method of treatment of an animal suffering from a disease mediated by cysteine protease activity, which method comprises administering to the mammal a sufficient amount of a compound of formula (I) as defined above to inhibit such activity.

Diseases mediated by cysteine protease activity include muscular dystrophy, osteoporosis, tumour metastasis, rheumatoid arthritis, neuronal or cardiac ischaemia, allergic immune response, and protozoal or bacterial disease.

Compositions with which the invention is concerned may be prepared for administration by any route consistent with the pharmacokinetic properties of the active ingredient(s).

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the active ingredients (s) may be made up into a cream, lotion or ointment. Cream or ointment formulations, which may be used for the drug, are conventional formulations well known in the art, for example as described in standard textbooks of pharmaceutics such as the British Pharmacopoeia.

The active ingredients(s) may also be administered parenterally in a sterile medium. Depending on the vehicle and concentration used, the drug can either be suspended or dissolved in the vehicle. Advantageously, adjuvants such as local anaesthetic, preservative and buffering agents can be dissolved in the vehicle. Intravenous infusion is another route of administration for the compounds.

Safe and effective dosages for different classes of patient and for different disease states will be determined by clinical trial as is required in the art. It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Compounds of the invention wherein A and B taken together represent a bond and $R_4$ represents $NH_2$ may be prepared by treatment of azetidin-2-ones of formula (IV) with ammonium hydroxide.

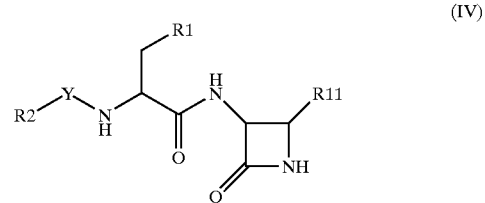

(IV)

wherein $R_{11}$ is a leaving group such as phenoxy, acetoxy.

Compounds of the invention wherein A and B taken together represent a bond and $R_4$ represents a primary or secondary amino group may be prepared by treatment of compounds (IV) with a primary or secondary amine, or by appropriate derivatisation of the amino group of the corresponding compounds wherein $R_4$ is amino.

Compounds of the invention wherein A and B taken together represent a bond and $R_4$ represents a hydroxy group may be prepared by treatment of compounds (IV) with acetic acid, for example at ambient temperatures. Compounds of the invention wherein A represents hydrogen and B and $R_4$ represents a hydroxy group may also be prepared by treatment of compounds (IV) with acetic acid, but under less forcing conditions than for the alpha-beta unsaturated compounds, for example at low temperatures such as about 0° C.

Compounds of the invention wherein A and B taken together represent a bond and R represents a substituted hydroxy group or a primary or secondary amino group may be prepared from the corresponding compounds wherein $R_4$ is hydroxy or amino by appropriate derivatisation of that hydroxy or amino group. Likewise, compounds of the invention wherein A represents hydrogen and B and $R_4$ are independently a substituted hydroxy group may be prepared from the corresponding compounds wherein B and $R_4$ are hydroxy by appropriate derivatisation of one or both of those hydroxy groups.

Compounds of the invention wherein A and B taken together represent a bond and $R_4$ represents an alkyl, alkenyl, alkynyl, cycloalkyl or aryl may be prepared by the following the synthetic scheme as depicted below in scheme 1.

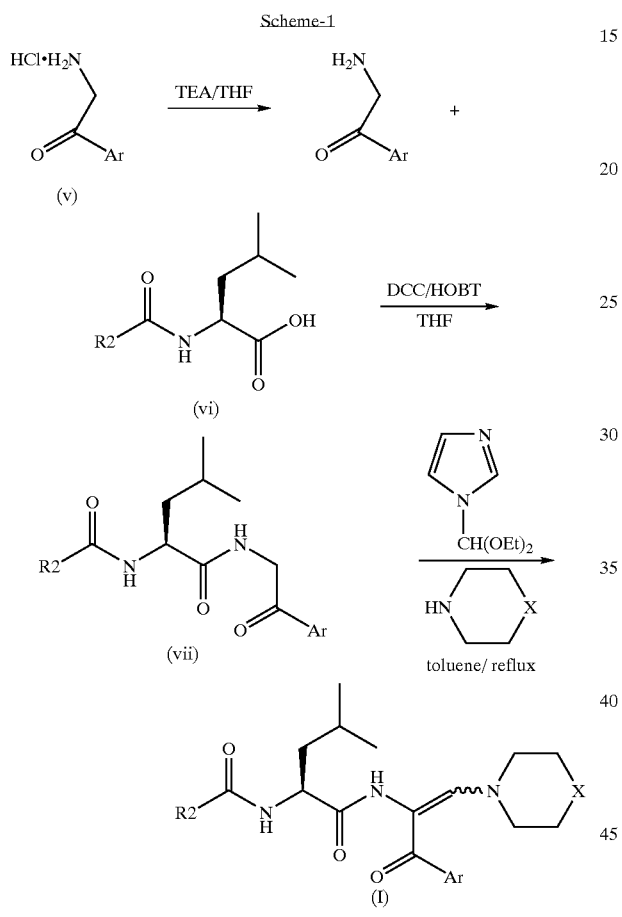

Compounds of the invention wherein A and B taken together represent a bond and $R_4$ represents an alkoxy, aryloxy or cycloalkoxy may be prepared by the following the synthetic scheme as depicted below in scheme 2.

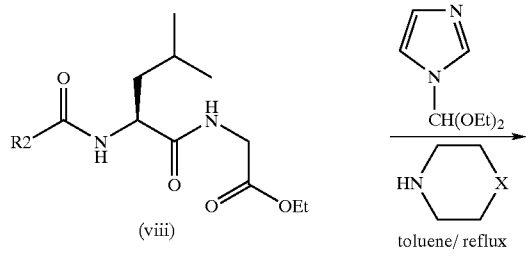

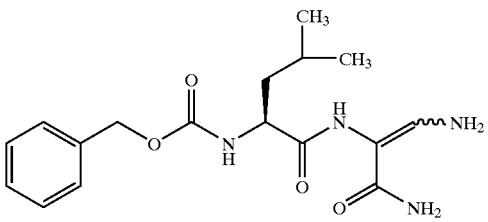

X = NH, O, NCH₃

In the above processes, the reactants are reacted together with solvent at elevated or low temperatures for sufficient time to allow the reaction to proceed to completion. The reaction conditions will depend upon the nature and reactivity of the reactants. Depending on the reactants, a solvent will generally be selected from the group consisting of benzene, toluene, acetonitrile, tetrahydrofuran, ethanol, methanol, chloroform, ethyl acetate, methylene chloride, dimethyl formamide, dimethyl sulfoxide, hexamethyl phosphoric triamide, water, pyridine, acetone and the like. Solvent mixtures may also be utilized.

Reaction temperatures generally range from between −70° C. to 150° C. The preferred molar ratios of reactants are 1:1 to 5. The reaction time range from 0.5 to 72 hours, depending on the reactants.

The azetidine-2-one strating materials (V) may be prepared by literature methods, including those in International patent applications WO 96/32408, WO 98/12176, WO 98/12210.

The following Examples illustrate embodiments of the invention.

EXAMPLE 1

2-(2S-2-Benzyloxycarbonylamino-2-isopropylmethyl-acetamido)-3-amino-acrylamide

A solution of (3S,4S)-3-(2S-2-benzyloxycarbonylamino-2-isopropylmethyl-acetamido)-4-acetoxy-azetidin-2-one (3.0 g, 7.6 mmole) in acetonitrile (50 ml) and 15 ml of ammonium hydroxide (28% $NH_3$ in water) was stirred at room temperature overnight. After removal of solvent under vacuum and lyophilization, the residue was purified by silica gel column chromatography using methanol-chloroform as eluant. 1.86 g of the title compound was obtained as white solid.

Yield: 70%; m.p.: 80–90° C. $^1$H-NMR: (DMSO-d$_6$), (ppm): 0.7–1.0 (6H, m), 1.4–1.75 (3H, m), 3.9–4.1 (1H, m), 5.02 (2H, s), 5.56 (1.4H, br), 6.26 (2H, s), 6.44 (0.3H, t, J=9 Hz), 6.95 (0.6H, br), 7.12 (0.7H, t, J=9 Hz), 7.25–7.45 (5H, m), 7.36 (0.3H, d, J=6.6 Hz), 7.62 (0.7H, d, J=6.6 Hz), 8.50 (0.7H, s), 8.67 (0.3H, s). MS (ES+): 349 (M+H), calcd for $C_{17}H_{24}N_4O_4$ 348.

EXAMPLE 2

2-(2S-2-Benzyloxycarbonylamino-2-cyclohexylmethyl-acetamido)-3-amino-acrylamide

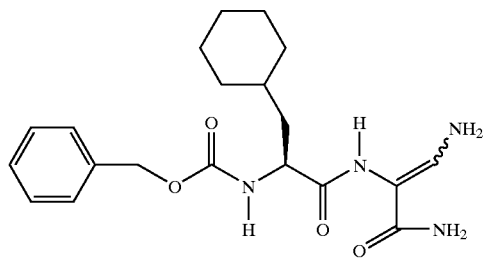

By a similar method as described in example 1, the title compound was obtained from (3S,4S)-3-(2S-2-benzyloxycarbonylamino-2-cyclohexylmethyl-acetamido)-4-acetoxy-azetidin-2-one.

Yield: 70%; m.p.: 80–85° C. $^1$H-NMR: (DMSO-d$_6$), (ppm): 0.7–1.95 (13H, m), 3.9–4.15 (1H, m), 5.01 (2H, s), 5.45–5.65 (1.6H, br), 6.26 (2H, s), 6.43 (0.2H, t, J=10 Hz), 6.9–7.0 (0.4H, br), 7.12 (0.8H, t, J=10 Hz), 7.3–7.45 (5H, m), 7.58 (0.2H, d, J=6.4 Hz), 7.62 (0.8H, d, J=6.4 Hz), 8.51 (0.8H, s), 8.66 (0.2H, s). MS (ES+): 389 (M+H), calcd for C$_{20}$H$_{28}$N$_4$O$_4$ 388.

EXAMPLE 3

2-(2S-2-Benzyloxycarbonylamino-2-benzyl-acetamido)-3-amino-acrylamide

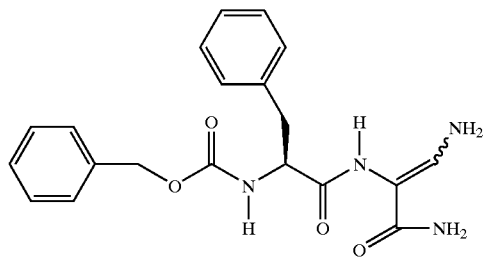

By a similar method as described in example 1, the title compound was obtained from (3S,4S)-3-(2S-2-benzyloxycarbonylamino-2-benzyl-acetamido)-4-acetoxy-azetidin-2-one.

Yield: 71%; m.p.: 127–135° C. $^1$H-NMR: (DMSO-d$_6$), (ppm): 2.8–3.2 (2H, m), 4.2–4.4 (1H, m), 4.97 (2H, s), 5.3–5.55 (2H, br), 6.10 (2H, s), 7.14 (1H, t, J=11 Hz), 7.2–7.4 (10H, m), 7.78 (1H, d, J=6.4 Hz), 8.6 (1H, s). MS (ES+): 383 (M+H), calcd for C$_{20}$H$_{22}$N$_4$O$_4$ 382.

EXAMPLE 4

2-[2S-2-(3-Phenylpropionoyl)amino-2-benzyl-acetamido]-3-amino-acrylamide

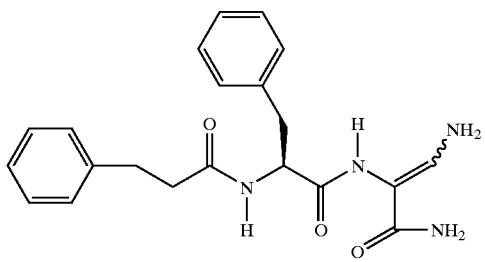

By a similar method as described in example 1, the title compound was obtained from (3S,4S)-3-[2S-2-(3-phenylpropionoyl)amino-2-benzyl-acetamido]-4-acetoxy-azetidin-2-one.

Yield: 75%; m.p.: 75–80° C. $^1$H-NMR: (DMSO-d$_6$), (ppm): 2.35–2.45 (2H, m), 2.70–3.15 (4H, m), 4.25–4.50 (1H, m), 5.25–5.50 (2H, br), 6.08 (2H, s), 7.06 (1H, t, J=11 Hz), 7.2–7.4 (10H, m), 8.32 (1H, d, J=6 Hz), 8.45 (1H, s). MS (ES+): 381 (M+H) calcd for C$_{21}$H$_{24}$N$_4$O$_3$ 380.

EXAMPLE 5

2-(2S-2-Benzyloxycarbonylamino-2-isopropylmethyl-acetamido)-3-benzylamino-acrylamide

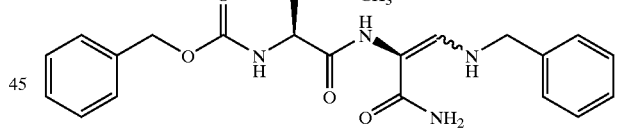

To a solution of (3S,4S)-3-(2S-2-benzyloxycarbonylamino-2-isopropylmethyl-acetamido)-4-acetoxy-azetidin-2-one (200 mg, 0.51 mmole) in acetonitrile (5 ml) and water (1 ml), benzylamine (542 mg, 5.1 mmole) was added and stirred at room temperature overnight. After removal of solvent under vacuum and lyophilization, the residue was purified by silica gel column chromatography using methanol-chloroform as eluant. 200 mg of the title compound was obtained as white solid.

Yield: 90%; m.p.: 115–120° C. $^1$H-NMR: (DMSO-d$_6$), (ppm): 0.8–1.8 (9H, m), 3.9–4.1 (1H, m), 4.29 (2H, d, J=5.5 Hz), 4.9–5.1 (2H, m), 5.9–6.1 (0.7H, m), 6.28 (2H, s), 6.61 (0.3H, d, J=12 Hz), 7.17 (0.7H, d, J=12 Hz), 7.25–7.45 (10H, m), 7.60 (0.3H, d, J=6.5 Hz), 7.66 (0.7H, d, J=6.5 Hz), 8.35–8.55 (0.3H, m), 8.60 (0.7H, s), 8.72 (0.3H, s). MS (ES+): 439 (M+H), calcd for C$_{24}$H$_{30}$N$_4$O$_4$ 438.

EXAMPLE 6

2-(2S-2-Benzyloxycarbonylamino-2-isopropylmethyl-acetamido)-3-(morpholin-4-yl)-acrylamide

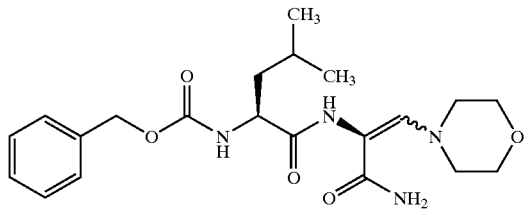

To a solution of (3S,4S)-3-(2S-2-benzyloxycarbonylamino-2-isopropylmethyl-acetamido)-4-acetoxy-azetidin-2-one (200 mg, 0.51 mmole) in acetonitrile (5 ml) and water (1 ml), morpholine (444 mg, 5.1 mmole) was added and stirred at room temperature overnight. After removal of solvent under vacuum and lyophilization, the solid was washed with ether. 200 mg of the title compound was obtained as white solid.

Yield: 90%; m.p.: 120–130° C. $^1$H-NMR: (DMSO-d$_6$), (ppm): 0.8–0.95 (6H, m), 1.3–1.75 (3H, m), 2.6–2.75 (4H, m), 3.5–3.6 (4H, m), 3.9–4.1 (1H, m), 5.00 (2H, s), 6.32 (2H, s), 7.07 (1H, s), 7.36 (5H, m), 7.67 (1H, d, J=6.7 Hz), 8.8 (1H, s). MS (ES+): 419 (M+H), calcd for C$_{21}$H$_{30}$N$_4$O$_5$ 418.

EXAMPLE 7

2-(2S-2-Benzyloxycarbonylamnino-2-isopropylmnethyl-acetamido)-3-(2-hydroxyethylamnino)-acrylamide

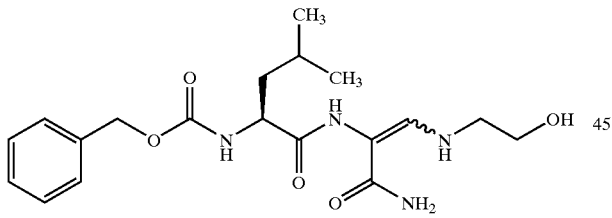

To a solution of (3S,4S)-3-(2S-2-benzyloxycarbonylamino-2-isopropylmethyl-acetamido)-4-acetoxy-azetidin-2-one (100 mg, 0.257 mmole) in acetonitrile (5 ml) and water (1 ml), hydroethylamine (32 mg, 0.53 mmole) was added and stirred at room temperature overnight. After removal of solvent under vacuum and lyophilization, the residue was purified by silica gel column chromatography using methanol-chloroform as eluant. 70 mg of the title compound was obtained as white solid.

Yield: 70%; m.p.: 89–92° C. $^1$H-NMR: (DMSO-d$_6$), (ppm): 0.8–0.95 (6H, m), 1.4–1.75 (3H, m), 3.05–3.2 (2H, m), 3.35–3.5 (2H, m), 3.95–4.1 (1H, m), 4.65 (1H, t, J=5 Hz), 5.02 (2H, s), 5.4–5.55 (1H, m), 6.75 (2H, s), 7.12 (1H, d, J=12 Hz), 7.35 (5H, m), 7.65 (1H, d, J=6 Hz), 8.55 (1H, s). MS (ES+): 393 (M+H), calcd for C$_{19}$H$_{28}$N$_4$O$_5$ 392.

EXAMPLE 8

2-(2S-2-Benzyloxycarbonylamino-2-isoproplmethyl-acetamido)-3-phenylamino-acrylamide

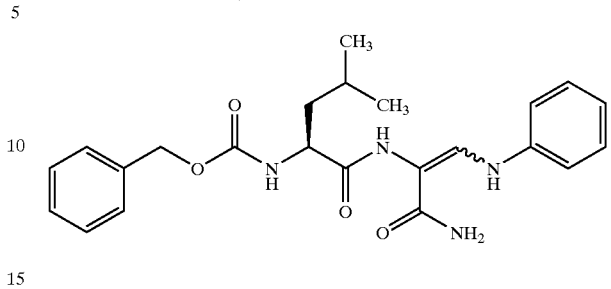

Aniline hydrochloride (500 mg, 3.8 mmole) was neutralised with Na$_2$CO$_3$ solution (600 mg, 5.7 mmole) and then extracted with ethyl acetate. After removal of solvent, aniline was dissolved in acetonitrile and added to a solution of (3S,4S)-3-(2S-2-benzyloxycarbonylamino-2-isopropylmethyl-acetamido)-4-acetoxy-azetidin-2-one (100 mg, 0.257 mmole) in acetonitrile (5 ml) and water (1 ml). The resulting mixture was stirred at room temperature overnight. After removal of solvent under vacuum and lyophilization, the residue was purified by silica gel column chromatography using methanol-chloroform as eluant. 10 mg of the title compound was obtained as white solid.

Yield: 10%; m.p.: 199–200° C. $^1$H-NMR: (DMSO-d$_6$), (ppm): 0.85–1.05 (6H, m), 1.5–1.8 (3H, m), 4.0–4.15 (1H, m), 5.09 (2H, s), 6.73 (2H, s), 6.88 (1H, t, J=7.2 Hz), 7.05 (2H, d, J=8 Hz), 7.24 (2H, d, J=7.5 Hz), 7.35 (5H, m), 7.7–7.9 (3H, m), 8.89 (1H, s). MS (ES+): 425 (M+H), calcd for C$_{23}$H$_{28}$N$_4$O$_4$ 424.

EXAMPLE 9

2-(2S-2-Benzyloxycarbonylamino-2-isopropylmethyl-acetamido)-3-piperidino-acrylamide

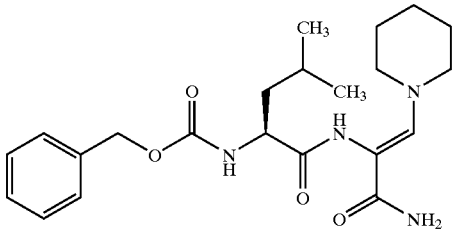

To a solution of (3S,4S)-3-(2S-2-benzyloxycarbonylamino-2-isopropylmethyl-acetamido)-4-acetoxy-azetidin-2-one (100 mg, 0.257 mmole) in acetonitrile (3 ml) and water (1 ml), piperidine (88 mg, 1.06 mmole) was added and stirred at room temperature overnight. After removal of solvent under vacuum and lyophilization, the residue was purified by silica gel column chromatography using methanol-chloroform as eluant. 70 mg of the title compound was obtained as white solid.

Yield: 70%; m.p.: 99–103° C. $^1$H-NMR: (DMSO-d$_6$), (ppm): 0.8–1.7 (15H, m), 3.2–3.3 (4H, m), 3.95–4.1 (1H, m), 5.01 (2H, s), 6.23 (2H, s), 7.08 (1H, s), 7.3–7.4 (5H, m), 7.63 (1H, d, J=6 Hz), 8.76 (1H, s). MS (ES+): 417 (M+H), calcd for C$_{22}$H$_{32}$N$_4$O$_4$ 416.

EXAMPLE 10a AND 10b (2E)-(2S-2-Benzyloxycarbonylamino-2-isopropylmethyl-acetamido)-3-acetamido-acrylamide (10a)

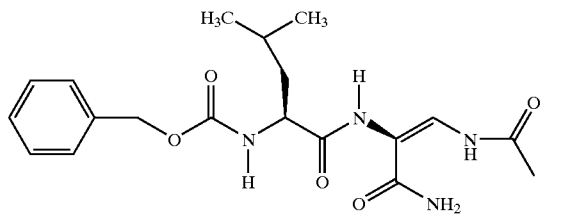

(2Z)-(2S-2-Benzyloxycarbonylamino-2-isopropylmethyl-acetamido)-3-acetamido-acrylamide (10b)

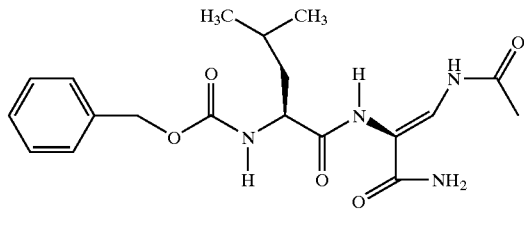

150 mg (0.43 mmole) of 2-(2S-2-benzyloxycarbonylamino-2-isopropylmethyl-acetamido)-3-amine-acrylamide (from example 1) was dissolved in acetic anhydride (5 ml) and stirred at room temperature for 2 days. After removal of acetic anhydride, the residue was purified by silica gel column chromatography using methanol-chloroform as eluant. 40 mg of the title compound (10a) and 45 mg of the title compound (10b) were obtained as white solid.

For (10a): Yield: 24%; m.p.: 73–76° C. $^1$H-NMR: (DMSO-d$_6$), (ppm): 0.8–1.0 (6H, m), 1.45–1.75 (3H, m), 2.08 (3H, s), 3.95–4.1 (1H, m), 5.02 (2H, s), 6.90 (1H, br), 7.08 (1H, d, J=12 Hz), 7.3–7.4 (5H, m), 7.5 (1H, br), 7.70 (1H, d, J=6 Hz), 9.23 (1H, s), 10.98 (1H, d, J=12 Hz). MS (ES+): 391 (M+H), calcd for $C_{19}H_{26}N_4O_5$ 390.

For (10b): Yield: 27%; m.p.: 120–123° C. $^1$H-NMR: (DMSO-d$_6$), (ppm): 0.8–1.0 (6H, m), 1.5–1.8 (3H, m), 2.01 (3H, s), 4.0–4.1 (1H, m), 5.06 (2H, s), 7.02 (2H, s), 7.3–7.45 (5H, m), 7.64 (1H, d, J=11.4 Hz), 7.84 (1H, d, J=6.2 Hz), 9.00 (1H, s), 9.13 (1H, d, J=11.4 Hz), MS (ES+): 391 (M+H), calcd for $C_{19}H_{26}N_4O_5$ 390.

EXAMPLE 11

2-(2S-2-Benzyloxycarbonylamino-2-isopropylmethyl-acetamido)-3,3-dihydroxy-propionamide

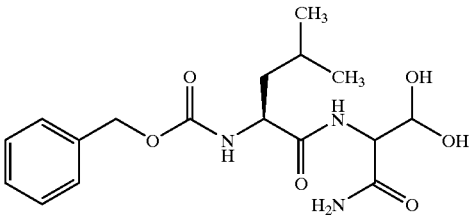

To a solution of 2-(2S-2-benzyloxycarbonylamino-2-isopropylmethyl-acetamido)-3-amine-acrylamide (30 mg, 0.086 mmole) (from example 1) in acetonitrile (2 ml) and water (0.5 ml), 5 drops of formic acid was added at 0° C. The mixture was stirred at 0° C. for 1 hr. After removal of acetonitrile under vacuum, precipitate was formed by addition of water (2 ml). The solid was purified by silica gel column chromatography using methanol-chloroform as eluant. 10 mg of the title compound was obtained as white solid.

Yield: 32%; m.p.: 86–90° C. $^1$H-NMR: (DMSO-d$_6$), (ppm): 0.8–1.0 (6H, m), 1.4–1.75 (3H, m), 4.0–4.3 (2H, m), 4.6–4.8 (1H, m), 5.02 (1H, s), 5.03 (1H, s), 6.35–6.45 (1H, m), 6.6–6.7 (1H, m), 7.2 (2H, br), 7.3–7.4 (5H, m), 7.5–7.9 (2H, m). MS (ES+): 350 (M–H$_2$O+H), calcd for $C_{17}H_{25}N_3O_6$ 367.

EXAMPLE 12

2-(2S-2-Benzyloxycarbonylamino-2-cyclohexylmethyl-acetamido)-3,3-dihydroxy-propionamide

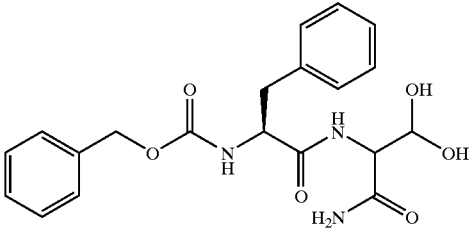

By a similar method as described in example 11, the title compound was obtained from 2-(2S-2-benzyloxycarbonylamino-2-cyclohexylmethyl-acetamido)-3-amino-acrylamide (from example 2).

Yield: 45%; m.p.: 105–110° C. $^1$H-NMR: (DMSO-d$_6$), (ppm): 0.8–1.8 (13H, m), 4.0–4.3 (2H, m), 4.6–4.85 (1H, m), 5.03 (2H, m), 6.3–6.7 (2H, m), 7.14 (2H, br), 7.3–7.4 (5H, m), 7.45–7.9 (2H, m). MS (ES+): 390 (M–H$_2$O+H), calcd for $C_{20}H_{29}N_3O_6$ 407.

EXAMPLE 13

2-(2S-2-Benzyloxycarbonylamino-2-benzyl-acetamido)-3,3-dihydroxy-propionamide

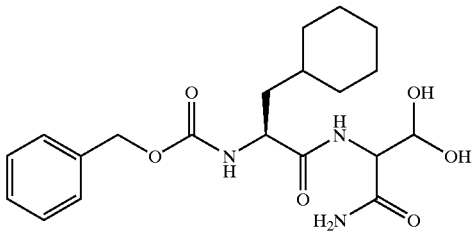

By a similar method as described in example 11, the title compound was obtained from 2-(2S-2-benzyloxycarbonylamino-2-benzyl-acetamido)-3-amino-acrylamide (from example 3).

Yield: 40%; m.p.: 98–103° C. $^1$H-NMR: (DMSO-d$_6$), (ppm): 2.7–3.15 (2H, m), 4.2–4.5 (2H, m), 4.65–4.8 (1H, m), 4.94 (2H, s), 6.35–6.5 (1H, m), 6.6–6.75 (1H, m), 7.1–7.45 (12H, m), 7.5–7.65 (1H, m), 7.9–8.15 (1H, m). MS (ES+): 384 (M–H$_2$O+H), calcd for C$_{20}$H$_{23}$N$_3$O$_6$ 401.

EXAMPLE 14

2-[2S-2-(3-Phenylpropionoylamino)-2-benzyl-acetamido]-3,3-dihydroxy-propionamide

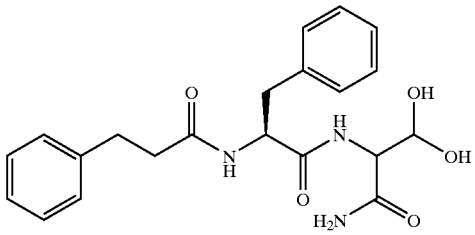

By a similar method as described in example 11, the title compound was obtained from 2-(2S-2-(3-phenylpropionoylamino)-2-benzyl-acetamido)-3-amino-acrylamide (from example 4).

Yield: 48%; m.p.: 105–110° C. $^1$H-NMR: (DMSO-d$_6$), (ppm): 2.3–2.4 (2H, m), 2.6–3.2 (4H, m), 4.2–4.3 (1H, m), 4.5–4.8 (2H, m), 6.3–6.45 (1H, m), 6.55–6.7 (1H, m), 7.1–7.45 (12H, m), 7.85–8.35 (2H, m). MS (ES+): 382 (M–H$_2$O+H), calcd for C$_{21}$H$_{25}$N$_3$O$_5$ 399.

EXAMPLE 15

2-(2S-2-Benzyloxycarbonylamino-2-isopropylmethyl-acetamido)-3-hydroxy-acrylamide

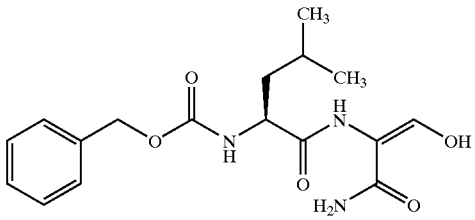

To a solution of 2-(2S-2-benzyloxycarbonylamino-2-isopropylmethyl-acetamido)-3-amine-acrylamide (55 mg, 0.158 mmole) (from example 1) in acetonitrile (3 ml) and water (0.5 ml), 10 drops of formic acid was added at 0° C. The mixture was stirred at room temperature for 1 hr. After removal of solvent under vacuum, the residue was purified by silica gel column chromatography using methanol-chloroform as eluant. 20 mg of the title compound was obtained as white solid.

Yield: 36%; m.p.: 105–115° C. $^1$H-NMR: (DMSO-d$_6$), (ppm): 0.8–1.0 (6H, m), 1.4–1.8 (3H, m), 3.9–4.15 (1H, m), 5.02 (2H, s), 6.5–7.1 (1.5H, m), 7.3–7.5 (7H, m), 7.65–7.8 (1H, m), 9.05 (1H, s), 10.2 (0.5H, m). MS (ES+): 350 (M+H), calcd for C$_{17}$H$_{23}$N$_3$O$_5$ 349.

EXAMPLE 16

2-(2S-2-Benzyloxycarbonylamino-2-isopropylmethyl-acetamido)-3-benzylamino-N-benzyl-acrylamide

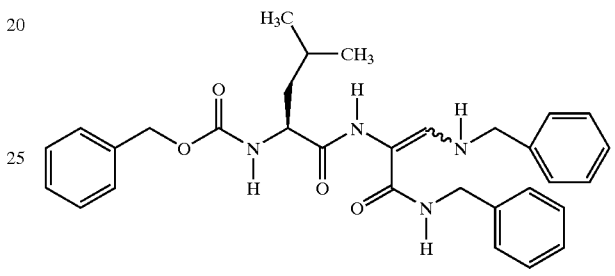

A solution of (3S,4S)-3-(2S-2-benzyloxycarbonylamino-2-isopropylmethyl-acetamido)-4-phenoxy-azetidin-2-one (1.1 g, 3.3 mmole) in ethanol (20 ml) and 5 ml of benzylamine -was stirred at room temperature overnight. After removal of solvent under vacuum and lyophilization, the residue was purified by silica gel column chromatography using methanol-chloroform as eluant. 0.96 g of the title compound was obtained as white solid.

Yield: 55%; $^1$H-NMR: (DMSO-d$_6$), (ppm): 0.8–1.0 (6H, m), 1.4–1.8 (3H, m), 3.9–4.1 (1H, m), 4.2–4.4 (4H, m), 4.7–4.9 (2H, m), 6.0–6.2 (0.5H, m), 6.6–6.8 (1H, m), 7.1–7.4 (16H, m), 7.6–7.8 (1H, m), 8.3–8.5 (0.5H, m), 8.68 (0.5H, s), 8.85 (0.5H, s). MS (ES+): 529 (M+H), calcd for C$_{32}$H$_{36}$N$_4$O$_4$ 528.

EXAMPLE 17

2-(2S-2-Benzyloxycarbonylamino-2-isopropylmethyl-acetamido)-3-(4-methylpiperazino)-acrylamide

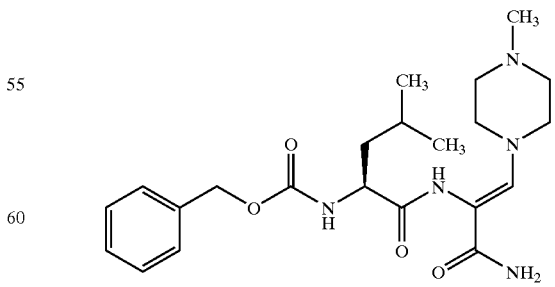

To a solution of (3S,4S)-3-(2S-2-benzyloxycarbonylamino-2-isopropylmethyl-acetamido)-4-acetoxy-azetidin-2-one (100 mg, 0.257 mmole) in acetonitrile (3 ml) and water (1 ml), 4-methylpiperazine (106 mg, 1.06 mmole) was added and stirred at room temperature overnight. After removal of acetonitrile under vacuum, the residue was dissolved in ethyl acetate and washed with water, brine and dried with $Na_2SO_4$. After removal of solvent, 30 mg of the title compound was obtained as white solid.

Yield: 27%; m.p.: 93.5–95° C. $^1$H-NMR: (DMSO-$d_6$), (ppm): 0.8–1.0 (6H, m), 1.3–1.8 (3H, m), 2.13 (3H, s), 2.2–2.35 (4H, m), 3.2–3.35 (4H, m), 3.95–4.1 (1H, m), 5.01 (2H, s), 6.29 (2H, s), 7.07 (1H, s), 7.3–7.4 (5H, m), 7.66 (1H, d, J=6.7 Hz), 8.79 (1H, s). MS (ES+): 432 (M+H), calcd for $C_{22}H_{33}N_5O_4$ 431.

EXAMPLE 18

2-(2S-2-Benzyloxycarbonylamino-2-isopropylmethyl-acetamido)-3-(3-tert-butoxycarbonylamino-pyrrolidino)-acrylamide

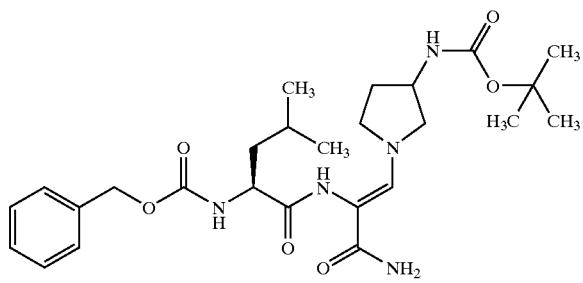

To a solution of (3S,4S)-3-(2S-2-benzyloxycarbonylamino-2-isopropylmethyl-acetamido)-4-acetoxy-azetidin-2-one (100 mg, 0.257 mmole) in acetonitrile (3 ml) and water (1 ml), 3-tert-butoxycarbonylamino-pyrrolidine (239 mg, 1.28 mmole) was added and stirred at room temperature overnight. After removal of acetonitrile under vacuum, the residue was dissolved in ethyl acetate and washed with water, brine and dried with $Na_2SO_4$. After removal of solvent, 120 mg of the title compound was obtained as white solid.

Yield: 90%; m.p.: 140–142° C. $^1$H-NMR: (DMSO-$d_6$), (ppm): 0.8–1.0 (6H, m), 1.3–2.0 (5H, m), 1.37 (9H, s), 3.0–3.2 (1H, m), 3.3–3.7 (3H, m), 3.9–4.1 (2H, m), 5.01 (2H, s), 6.25 (2H, s), 7.12 (1H, d, J=6.5 Hz), 7.22 (1H, s), 7.3–7.4 (5H, m), 7.66 (1H, d, J=6.5 Hz), 8.75 (1H, s). MS (ES+): 518 (M+H), calcd for $C_{26}H_{39}N_5O_6$ 517.

EXAMPLE 19a AND 19b (2E)-(2S-2-Benzyloxycarbonylamino-2-cyclohexymethyl-acetamido)-3-acetamido-acrylamide (19a)

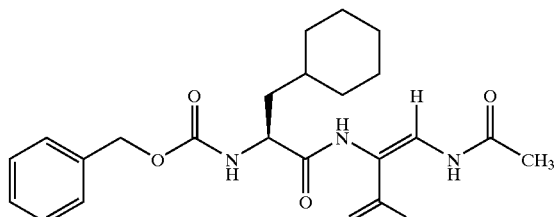

(2Z)-(2S-2-Benzyloxycarbonylamino-2-cyclohexylmethyl-acetamido)-3-acetamido-acrylamide (19b)

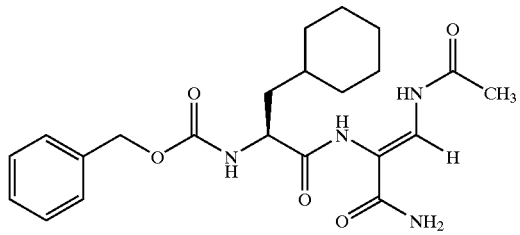

By a similar method as described in example 10, the title compound was obtained from 2-(2S-2-benzyloxycarbonylamino-2-cyclohexylmiethyl-acetamido)-3-amino-acrylamide (example 2).

For (19a): Yield: 21%; m.p.: 140–142° C. $^1$H-NMR: (DMSO-$d_6$), (ppm): 0.7–1.8 (13H, m), 2.01 (3H, s), 3.95–4.1 (1H, m), 5.02 (2H, m), 6.88 (1H, br), 7.07 (1H, d, J=11 Hz), 7.3–7.4 (5H, m), 7.5 (1H, br), 7.65 (1H, d, J=6 Hz), 9.20 (1H, s), 10.97 (1H, d, J=11 Hz). MS (ES+): (M+H), calcd for $C_{22}H_{30}N_4O_5$ 430.

For (19b): Yield: 41%; m.p.: 151–153° C. $^1$H-NMR: (DMSO-$d_6$), (ppm): 0.8–1.8 (13H, m), 1.99 (3H, s), 4.0–4.1 (1H, m), 5.04 (2H, m), 7.01 (2H, br), 7.3–7.4 (5H, m), 7.62 (1H, d, J=11.4 Hz), 7.81 (1H, d, J=6.2 Hz), 8.98 (1H, s), 9.11 (1H, d, J=11.4 Hz), MS (ES+): (M+H), calcd for $C_{22}H_{30}N_4O_5$ 430.

EXAMPLE 20 tert-Butyl-2-[2S-(benzyloxycarbonylamino)-2-isopropylmethyl-acetamido]-2-(morpholino-1-methylenyl)-acetate (20)

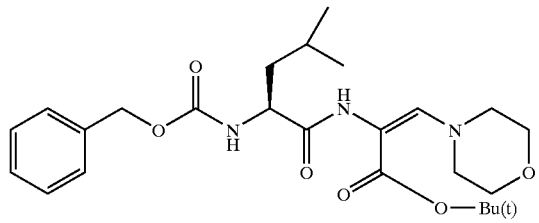

A mixture of ZLeuGlyOBu$^t$ (0.5 g, 0 mmol), 1-(diethoxymethyl)imidazole (0.36 g, mmol) and camphor shulphonic acid (0.056 g, mmol) in toluene was treated with morpholine (1.0 ml, mmol) and was refluxed for 24 hrs. Solvent was removed in vacuo and the crude product obtained was purified over silica gel column chromatography using a gradient mixture of hexane and ethyl acetate (1:1 to 2:1) gave 20 mg of title compound.

Yield; 3.2%; $^1$H NMR: (DMSO-$d_6$): δ 0.80–0.90 (m, 6H), 1.24–1.72 (m, 3H), 3.2–3.48 (m, 8H), 3.95–4.06 (m, 1H), 5.00 (AB$_q$, 2H, J=2.7 and 13.0 Hz), 7.11 (s, 1H), 7.34 (s, 5H), 7.43 (d, 1H, J=8.0 Hz), 8.49 (s, 1H).

EXAMPLE 21

Ethyl-2-[2S-(benzyloxycarbonylamino)-2-isopropylmethyl-acetamido]-2-(4-methylpiperazino-1-methylenyl)-acetate (21)

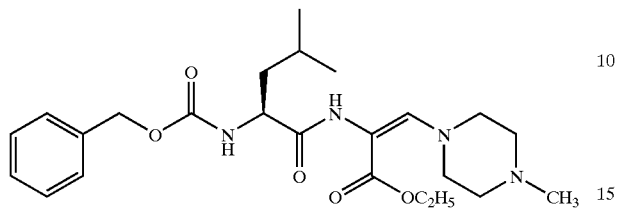

A mixture of ZLeuGlyOEt (0.3 g, 0.86 mmol), 1-(diethoxymethyl)imidazole (0.28 g, 1.27 mmol) in toluene was treated with N-methylpiperazine(0.94 ml, 8.5 mmol) and was refluxed for 24 hrs. Solvent was removed in vacuo and the crude product obtained was purified over. Purification of the above crude product over silica gel column chromatography using a mixture of ethyl acetate and methanol (9:1) gave the title compound (0.025 g), Yield 6.3%, m.p. 184° C. $^1$H NMR: (DMSO-$d_6$): δ 0.87–0.95 (m, 6H), 1.12 (t, 3H, J=7.0 Hz), 1.43–1.79 (m, 3H), 2.11 (s, 3H), 2.21 (s, 4H), 3.40 (m, 4H), 3.94 (q, 2H, J=7.0 Hz), 3.97–4.12 (m, 1H), 5.01 (AB$_q$, 2H, J=8.3 and 12.6 Hz), 7.20 (s, 1H), 7.34 (s, 5H), 7.44 (d, 1H, J=7.9 Hz), 8.53 (s, 1H).

EXAMPLE 22

Ethyl-2-[2S-(benzyloxycarbonylamino)-2-phenylmethyl-acetamido]-2-(morpholino-1-methylenyl)-acetate (22)

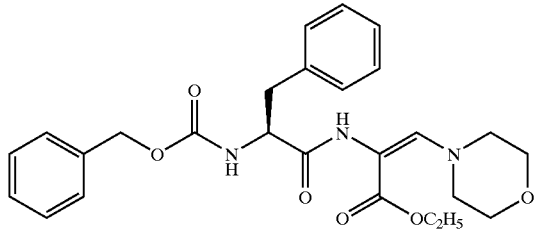

By a similar method as described in example 21, the title compound compound was obtained from Ethyl-2-[2S-(benzyloxycarbonylamino)-2-phenylmethyl-acetamido]-acetate, morpholine and 1-(diethoxymethyl)imidazole.

Yield; 4.5%, m.p. 215–217° C.; $^1$H NMR: (DMSO-$d_6$): δ 1.14 (t, 3H, J=7.1 Hz), 2.69–3.10 (m, 2H), 3.35–3.47 (m, 8H), 3.98 (q, 2H, J=6.2 Hz), 4.20–4.33 (m, 1H), 4.93 (AB$_q$, 2H, J=6.7 and 12.7 Hz), 7.20–7.40 (m, 11H), 7.57 (d, 1H, J=8.4 Hz), 8.79 (s, 1H).

EXAMPLE 23

Ethyl-2-[2S-(benzyloxycarbonylamino)-2-isopropylmethyl-acetamido]-2-(morpholino-1-methylenyl)-acetate (23)

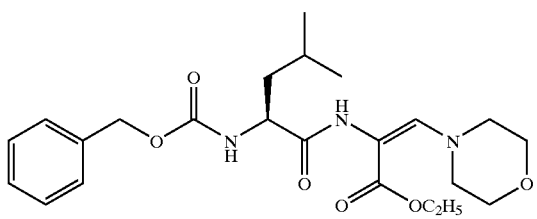

By a similar method as described in example 21, the title compound compound was obtained from Ethyl-2-[2S-(benzyloxycarbonylamino)-2-isopropylmethyl-acetamido]-acetate, morpholine and 1-(diethoxymethyl)imidazole Yield; 16%, m.p. 139–141° C.; $^1$H NMR: (DMSO-$d_6$): δ 0.87 (t, 6H, J=6.1 Hz), 1.13 (t, 3H, J=7.1 Hz), 1.43–1.78 (m, 3H), 3.38–3.51 (m, 8H), 3.90–4.09 (m, 3H), 5.00 (AB$_q$, 2H, J=2.1 and 12.7 Hz), 7.21 (s, 1H), 7.34 (s, 5H), 7.45 (d, 1H, J=7.5 Hz), 8.56 (s, 1H).

EXAMPLE 24

Ethyl-2-[2S-(benzyloxycarbonylamino)-2-cyclohexylmethyl-acetamido]-2-(morpholino-1-methylenyl)-acetate (24)

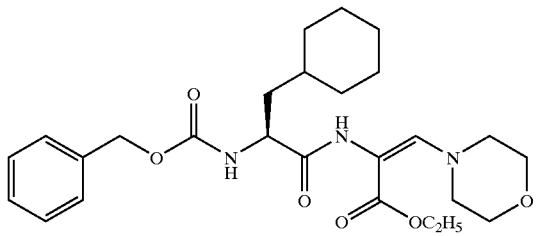

By a similar method as described in example 21, the title compound compound was obtained from Ethyl-2-[2S-(benzyloxycarbonylamino)-2-cyclohexylmethyl-acetamido]-acetate, morpholine and 1-(diethoxymethyl)imidazole.

Yield; 10%, m.p. 202° C. $^1$H NMR: (DMSO-$d_6$): δ 0.75–1.76 (m, 16H), 3.35–3.50 (m, 8H), 3.90–4.12 (m, 3H), 5.00 (s, 2H), 7.21 (s, 1H), 7.34 (s, 5H), 7.45 (d, 1H, J=7.0 Hz), 8.54 (s, 1H).

EXAMPLE 25

Diphenylmethyl-2-[2S-(3-phenylpropionylamino)-2-phenylmethyl-acetamido]-2-(morpholino-1-methylenyl)-acetate

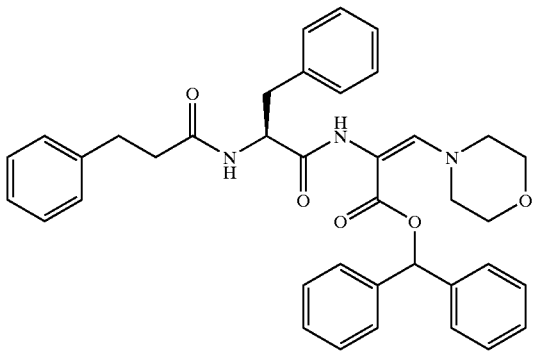

By a similar method as described in example 21, the title compound compound was obtained from Diphenylmethyl-2-[2S-(benzyloxycarbonylamino)-2-isopropylmethyl-acetamido]-acetate, morpholine and 1-(diethoxymethyl) imidazole.

Yield; 27%, m.p. 167–170° C.; $^1$H NMR: (DMSO-d$_6$): 2.32 (t, 2H, J=8.4 Hz), 2.67 (t, 2H, J=7.0 Hz), 2.70–3.26 (m, 2H), –3.40–3.55 (m, 8H), 4.50–4.67 (m, 1H), 6.74 (s, 1H), 7.10–7.49 (m, 20H), 8.27 (d, 1H, J=8.0 Hz), 8.95 (brs, 1H).

EXAMPLE 26

2-[2S-(Benzothiophen-2-carbonylamino)-2-isopropylmethyl-acetamido]-2-(morpholino-1-methylenyl)-4'-methoxyacetophenone (26)

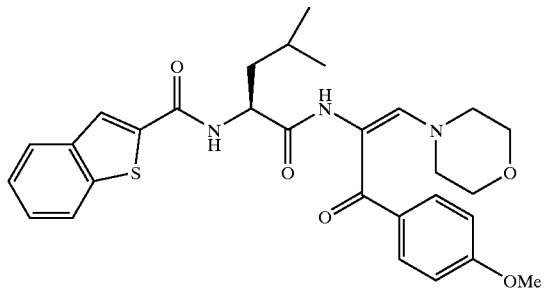

A mixture of N-(benzothiophene-2carbonyl)amino-Leucine (0.332 g, 1.14 mmol), DCC(0.235 g, 1.14 mmol) and 1-hydroxy benzotriazole (0.154 g, 1.14 mmol) in dry THF was stirred under nitrogen at r.t. for 1 h and cooled to 0° C. The suspension obtained was filtered and to the filtrate was added 2-amino-4'-methoxy acetophenone (0.23 g, 1.14 mmol) followed by triethyl amine (0.127 g, 1.25 mmol). The reaction mixture was stirred at r.t. for 6 hrs. and evaporated in vacuo to give the crude product. Purification of the above crude product over silica gel column chromatography using a mixture of hexane and ethyl acetate (2:3) gave 288 mg of title compound 2[2S-(benzothiophene-2-carbonyl)amino-2-isopropylmethyl-acetamido]-(4'-methoxy)acetophenone.

Yield; 58%, $^1$H NMR: (DMSO-d$_6$): δ 0.90–1.00 (m, 6H), 1.58–1.82 (m, 3H), 3.84 (s, 3H), 4.55–4.67 (m, 3H), 7.05 (d, 2H, J=8.8 Hz), 7.44–7.48 (m, 2H), 7.95–8.05 (m, 4H), 8.28 (s, 1H), 8.35 (t, 1H, J=5.9 Hz), 8.86 (d, 1H, J=8.3 Hz).

A mixture of 2-[2S-(benzothiophene-2-carbonyl)-amino-2-isopropylmethyl-acetamido]-4'-methoxyacetophenone (0.271 g, 0.618 mmol) and 1-(diethoxymethyl)imidazole (0.202 g, 0.927 mmol) in toluene was treated morpholine (0.269 g, 3.09 mmol) and refluxed at 130° C. over 22 hrs. Toluene was removed in vacuo and the crude product was purified over silica gel column chromatography using a mixture of ethyl acetate and methanol (9:1) to give 200 mg of title compound.

Yield: 60%, m.p. 134–136° C.; $^1$H NMR: (DMSO-d$_6$): δ0.82–0.93 (m, 6H), 1.15–1.87 (m, 3H), 3.40–3.56 (m, 8H), 3.75 (s, 3H), 4.37–4.50 (m, 1H), 6.90 (d, 2H, J=8.6 Hz), 7.09 (s, 1H), 7.41–7.47 (m, 4H), 7.95–8.05 (m, 2H), 8.25 (s, 1H), 8.81 (d, 1H, J=7.7 Hz), 8.98 (s, 1H).

EXAMPLE 27

2-[2S-(Benzyloxycarbonylamino)-2-isopropylmethyl-acetamido]-2-(morpholino-1-methylenyl)-acetophenone (27)

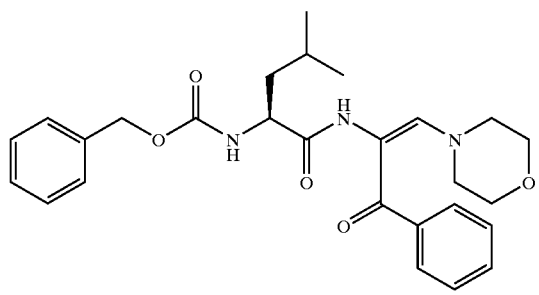

By following the procedure as described in example 25, the title compound was obtained from 2-[2S-(Benzyloxycarbonylamino)-2-isopropylmethyl-acetamido]-acetophenone, morpholine and 1-(diethoxymethyl) imidazole.

Yield; 53%, m.p. 107–109° C.; $^1$H NMR: (DMSO-d$_6$): δ 0.78–0.85 (m, 6H), 1.06–1.63 (m, 3H), 3.40–3.55(m, 8H), 3.90–4.05 (m, 1H), 5.00 (AB$_q$, 2H, J=2.0 and 10.7 Hz), 7.13 (s, 1H), 7.35 (s, 5H), 7.38s, 5H), 7.44 (d, 1H, J=8.0 Hz), 8.81 (s, 1H).

EXAMPLE 28

2-[2S-(Benzyloxycarbonylamino)-2-isopropylmethyl-acetamido]-2-(morpholino-1-methylenyl)-4'-methoxyacetophenone (28)

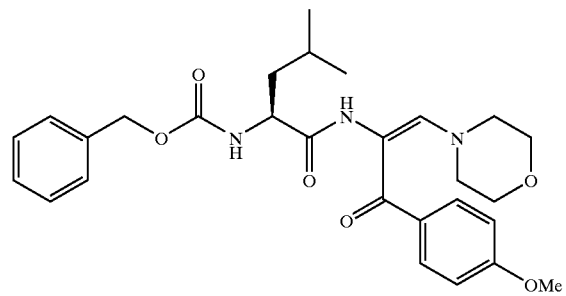

By following the procedure as described in example 25, the title compound was obtained from 2-[2S-(Benzyloxycarbonylamino)-2-isopropylmethyl-acetamido]-4'-methoxyacetophenone, morpholine and 1-(diethoxymethyl)imidazole.

Yield; 53%, m.p. 140–143° C.; ¹H NMR: (DMSO-d₆): δ 0.77–0.85 (m, 6H), 1.17–1.63 (m, 3H), 3.40–3.53 (m, 8H), 3.75 (s, 3H), 3.90–4.05 (m, 1H), 4.99 (s 2H), 6.89 (d, 2H, J=8.6 Hz), 7.07 (s, 1H), 7.33–7.45 (s, 8H), 8.80 (s, 1H).

EXAMPLE 29

2-[2S-(Benzyloxycarbonylamino)-2-isopropylmethyl-acetamido]-2-(morpholino-1-methylenyl)-4'-fluoroacetophenone (29)

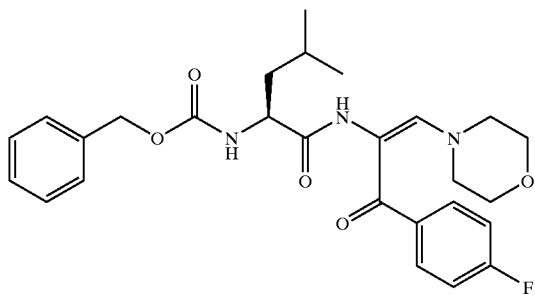

By following the procedure as described in example 25, the title compound was obtained from 2-[2S-(Benzyloxycarbonylamino)-2-isopropylmethyl-acetamido]-4'-fluoroacetophenone, morpholine and 1-(diethoxymethyl) imidazole.

Yield; 30%, m.p. 156–157° C.; ¹H NMR: (DMSO-d₆): δ 0.80–0.90 (m, 6H), 1.05–1.64 (m, 3H), 3.50 (m, 8H), 3.87–4.03 (m, 1H), 5.00 (s, 2H), 7.15–7.50 (m, 11H), 8.85 (s, 1H).

EXAMPLE 30a AND 30b (2E)-(2S-2-Benzyloxycarbonylamino-2-phenylmethyl-acetamido)-3-(1-carbomethoxy-2-phenethylamino)-acrylamide (30a)

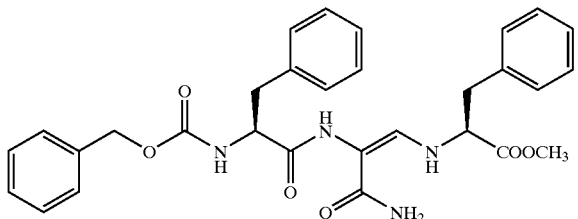

(2Z)-(2S-2-Benzyloxycarbonylamino-2-phenylmethyl-acetamido)-3-(1-carbomethoxy-2-phenethylamino)-acrylamide (30b)

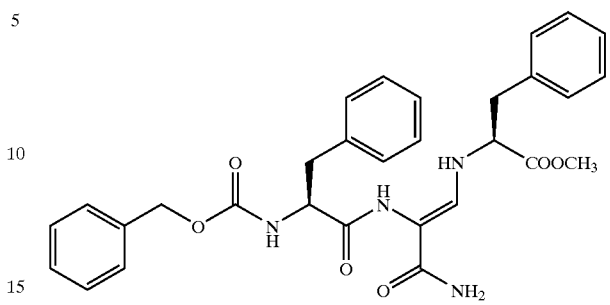

By following the procedure as described in example 18, the title compounds were obtained from (3S,4S)-3-(2S-2-benzyloxycarbonylamino-2-isopropylmethyl-acetamido)-4-acetoxy-azetidin-2-one and methyl ester of phenylalanine.

For 30a: Yield; 34%, m.p. 71–73° C.; NMR (DMSO-d₆): 2.75–3.03 (m, 4H), 3.63 (s, 3H), 4.12–4.38 (m, 2H), 4.96 (s, 2H), 6.00 and 6.55 (2br. s, 2H), 6.34 (d, 1H, J=12.2 Hz), 7.20–7.46 (m, 15H), 7.67 (d, 1H, J=6.0 Hz), 8.30–8.40 (m, 1H), 8.70 (s, 1H).

For 30b: Yield; 42%, m.pt. 85–87° C.; NMR (DMSO-d₆): 2.79–3.15 (m, 4H), 3.60 (s, 3H), 4.16–4.35 (m, 2H), 4.96 (AB$_q$, 2H, J=2.2 and 12.6 Hz), 5.42–5.53 (m, 1H), 6.15 (brs, 2H), 7.08 (d, 1H, J=13.0 Hz), 7.20–7.30 (m, 15H), 7.79 (d, 1H, J=6.5 Hz), 8.71 (s, 1H).

EXAMPLE 31a AND 31b (2E)-(2S-2-Benzyloxycarbonylamino-2-phenylmethyl-acetamido)-3-(1-carbomethoxy-methylamino)-acrylamide (31a)

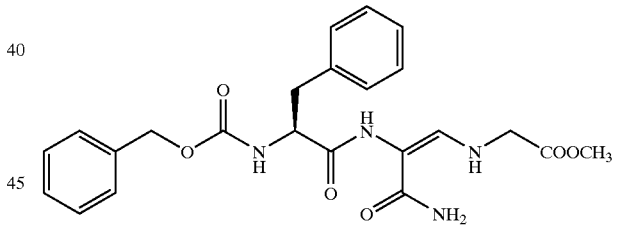

(2Z)-(2S-2-Benzyloxycarbonylamino-2-phenylmethyl-acetamido)-3-(1-carbomethoxy-methylamino)-acrylamide (31b)

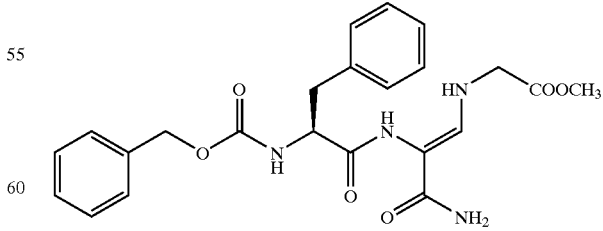

By following the procedure as described in example 18, the title compounds were obtained from (3S,4S)-3-(2S-2-benzyloxycarbonylamino-2-isopropylmethyl-acetamido)-4-acetoxy-azetidin-2-one and methyl ester of glycine For 31a: Yield; 36%, m.p. 108–110° C.; NMR (DMSO-d₆): 1.21 (t, 3H, J=7.0 Hz), 2.76–3.04 (m, 2H), 3.94 (d, 2H, J=6.2 Hz), 4.11 (q, 2H, J=7.0 Hz), 4.11–4.25 (m, 1H), 4.96 (s, 2H), 6.02 and 6.53 (2brs, 2H), 6.30 (d, 1H, J=12.5 Hz), 7.26–7.35 (m, 10H), 7.67 (d, 1H, J=6.9 Hz), 8.12–8.25 (m, 1H), 8.72 (s, 1H).

For 31b: Yield; 41%, m.p. 145–147° C.; NMR (DMSO-d₆): 1.20 (t, 3H, J=7.4 Hz), 2.75–3.15 (m, 2H), 3.88 (d, 2H, J=5.9 Hz), 4.16 (q, 2H, J=7.4 Hz), 4.25–4.87 (m, 1H), 4.98 (s, 2H), 5.22–5.35 (m, 1H), 6.20 (brs, 1H), 7.05 (d, 1H, J=11.8 Hz), 7.19–7.35 (m, 10H), 7.75 (d, 1H, J=6.6 Hz), 8.70 (s, 1H).

BIOLOGICAL EXAMPLE

Testing of Inhibitors for Inhibition of Cathepsin B, L, K and S

In Vitro Assay Procedure for Cathepsin B

The compounds of formula I were tested for inhibition of cathepsin B using the known method (A. J. Barret et al., Biochem. J. 1982, 201, 189–198). To a 170 μl of enzyme-buffer mixture (enzyme: r rat cathepsin B, diluted to give approximate 10 F units/min, buffer: 56 mM sodium acetate, 1.124 mM EDTA, 10 mM DTT, pH 5.1) a 10 μL of inhibitor (dissolved in DMSO) was added. After 10 min of incubation at room temperature, a 20 μl of 5 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and $IC_{50}$ is determined using a linear regression calculations (concentration of inhibitor which will give 50% inhibition).

In Vitro Assay Procedure for Cathepsin L

To a 170 μl of enzyme-buffer mixture (enzyme: r rat cathepsin L, diluted to give approximate 15 F units/min, buffer: 58.8 mM sodium citrate, 1.18 mM EDTA, 235 mM sodium chloride, 5 mM UT, pH 5.0) a 10 μL of inhibitor (dissolved in DMSO) was added. After 10 min of incubation at room temperature, a 20 μl of 1 mM substrate (N-CBZ-Phe-Arg-AMC, dissolved in DMSO) was added to initiate reaction. Reading is followed up for 10 min at the fluoroscan reader (excitation at 380 nm emission at 460 nm).

A plot of percentage of inhibition vs inhibitor concentration is obtained, and $IC_{50}$ is determined using a linear regression calculations (concentration of inhibitor which will give 50% inhibition).

In Vitro Assay Procedure for Cathepsin K

To a 170 μl of enzyme-buffer mixture (enzyme: r cathepsin K, diluted to give approximate 30 F units/min, buffer: 100 mM sodium acetate, 5 mM EDTA, 20 mM L-cysteine, 0.01% Brij, pH 5.5) a 10 μL of inhibitor (dissolved in DMSO) was added. After 10 min of incubation at room temperature, a 20 μl of 2.7 mM substrate (N-CBZ-Phe-Arg-AMC, dissolved in DMSO) was added to initiate reaction. Reading is followed up for 10 min at the fluoroscan II plate reader (excitation at 380 nm emission at 460 nm).

A plot of percentage of inhibition vs inhibitor concentration is obtained, and $IC_{50}$ is determined using a linear regression calculations (concentration of inhibitor which will give 50% inhibition).

In Vitro Assay Procedure for Cathepsin S

To a 170 μl of enzyme-buffer mixture (enzyme: r cathepsin S, diluted to give approximate 30 F units/min, buffer: 100 mM sodium phosphate, 1 mM EDTA, 5 mM DTT, 0.01% Brij, pH 6.5) a 10 μL of inhibitor (dissolved in DMSO) was added. After 10 min of incubation at room temperature, a 20 μl of 1.2 mM substrate (N-CBZ-Val-Val-Arg-AMC, dissolved in DMSO) was added to initiate reaction. Reading is followed up for 10 min at the fluoroscan II plate reader (excitation at 380 nm emission at 460 nm).

A plot of percentage of inhibition vs inhibitor concentration is obtained, and $IC_{50}$ is determined using a linear regression calculations (concentration of inhibitor which will give 50% inhibition).

TABLE 1

In vitro inhibitory activity of compounds on cysteine proteases

| | $IC_{50}$ (μM) | | | |
|---|---|---|---|---|
| Example No. | Cathepsin B | Cathepsin L | Cathepsin K | Cathepsin S |
| 1 | 4.35 | 0.094 | 0.011 | 0.069 |
| 2 | 1.17 | 0.072 | 1.78 | 0.026 |
| 3 | 1.42 | 0.0055 | 0.23 | 0.26 |
| 4 | 2.63 | 0.015 | 1.2 | 0.0087 |
| 5 | 2.28 | 0.064 | 0.0031 | 0.061 |
| 6 | 0.37 | 0.075 | 0.003 | 0.05 |
| 7 | 1.96 | 0.23 | 0.012 | 0.18 |
| 8 | 37.1 | 2.36 | 0.33 | 6.9 |
| 9 | 0.89 | 0.062 | 0.014 | 0.05 |
| 10a | 45.21 | 8.62 | 1.42 | 0.013 |
| 10b | 50.51 | >64 | 10.73 | >3.2 |
| 11 | 2.4 | 0.11 | 0.014 | 0.015 |
| 12 | 1.64 | 0.076 | 2.06 | 0.0035 |
| 13 | 1.4 | 0.004 | 0.4 | 0.004 |
| 14 | 0.98 | 0.004 | 1.13 | 0.004 |
| 15 | 9.5 | 0.17 | 0.018 | 0.075 |
| 16 | 0.15 | 0.015 | 0.01 | 0.026 |
| 17 | 1.9 | 0.23 | 0.019 | 0.18 |
| 18 | 1.9 | 0.12 | 0.0096 | 0.039 |
| 19a | >58 | >58 | >58 | 1.86 |
| 19b | >58 | 58 | >58 | 5.23 |
| 20 | 0.42 | 0.08 | 0.004 | 0.38 |
| 21 | 8.21 | 0.21 | 0.087 | 0.3 |
| 22 | 0.08 | 0.04 | 0.04 | 0.42 |
| 23 | 0.45 | 0.089 | 0.011 | 0.038 |
| 24 | 0.082 | 0.082 | 0.37 | 0.0033 |
| 25 | 0.06 | 0.18 | 0.065 | 0.18 |
| 26 | 1.47 | 0.075 | 0.015 | 0.99 |
| 27 | 32.27 | 4.24 | 0.14 | 52.2 |
| 28 | 1.96 | 0.27 | 0.016 | 1.3 |
| 29 | 50.3 | 2.01 | 0.34 | 50.3 |
| 30a | 1.83 | 0.048 | 0.28 | 0.57 |
| 30b | 1.83 | 0.035 | 0.28 | 1.21 |
| 31a | 0.66 | 0.017 | 0.13 | 0.7 |
| 31b | 0.43 | 0.017 | 0.09 | 0.43 |

What is claimed is:

1. A compound of formula (I)

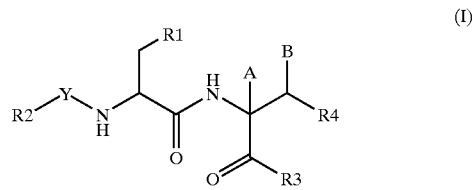

wherein:

Y represents —C(O)— or —S(O₂)—;

R₁ represents a radical of formula R₆—(ALK)ₚ—(Z)ₙ—(ALK)_q— wherein Z represents —O— or —S—, ALK represents a divalent C₁–C₃alkyl or halogen-substituted C₁–C₃alkyl radical, p and q are independently 0 or 1, n is 0 or 1 when q is 1 and n is 0 when q is 0, and R₆ is hydrogen or an optionally substituted C₁–C₆alkyl, C₂–C₆alkenyl, C₂–C₆alkynyl, cycloalkyl, cycloalkenyl or heterocyclic group; or R₁ together with the carbon atom to which it is attached forms a cycloalkyl ring;

$R_2$ represents —$OR_5$ or —$R_5$;

$R_5$ represents a radical of formula $R_7$—$(A)_t$— wherein t is 0 or 1; A represents (i) an optionally substituted divalent $C_1$–$C_6$alkyl, radical which may be interrupted by one or more non-adjacent —O—, —S— or —NH— linkages, or (ii) a divalent $C_2$–$C_6$alkenyl, $C_2$–$C_6$alkynyl, cycloalkyl, cycloalkenyl, aryl or heterocyclic radical, or (iii) a —NH— link; and $R_7$ represents hydrogen or an optionally substituted $C_1$–$C_6$alkyl, $C_2$–$C_6$alkenyl, $C_2$–$C_6$alkynyl, cycloalkyl, cycloalkenyl, aryl or heterocyclic group;

$R_3$ represents (I) an optionally substituted $C_1$–$C_6$alkyl, $C_2$–$C_6$alkenyl, $C_2$–$C_6$alkynyl, cycloalkyl, cycloalkenyl, aryl or heterocyclic group or (ii) $NHR_8$ or $N(R_8)_2$ or (iii) $OR_8$ wherein $R_8$ represents hydrogen or an optionally substituted propyl, isopropyl, butyl, $C_5$–$C_6$alkyl, $C_2$–$C_6$alkenyl, $C_2C_6$alkynyl, cycloalkyl, cycloalkenyl or;

A and B taken together represent a bond and $R_4$ represents a hydroxy or substituted hydroxy group or an amino or primary or secondary amino group, or A represents hydrogen and B and $R_4$ each independently represents a hydroxy or substituted hydroxy group;

or a pharmaceutically acceptable salt, hydrate or solvate thereof.

2. A compound as claimed in claim 1 wherein Y is —C(O)—.

3. A compound as claimed in claim 1 wherein $R_1$ is an isopropyl; cyclohexyl; 3-pyridinyl; naphthyl; biphenyl; 2-thienyl; 3,4-methylenedioxyphenyl; 3,4-ethylenedioxyphenyl; benzothienyl; thiazolyl; quinolinyl; isoquinolinyl; tetrahydroquinolinyl; tetrahydronaphthyl; aminonaphthyl; or acetamidonaphthyl group.

4. A compound as claimed in claim 1 wherein $R_2$ is benzyloxy, 3-phenylpropyloxy, 3-phenylpropyl, 3-phenylprop-enyl, 6-N,N dibenzyloxy-carbonylguanidino hexyl, 6-guanidino-hexyl, methoxy-methyleneoxy-methyl, 2-amino-ethoxy-methyl, 3-(pyridin-3- or 4-yl)-propyl, or 3-(pyridin-3- or 4-yl)-prop-1-enyl.

5. A compound as claimed in claim 1 wherein $R_3$ is selected from methyl, ethyl, isopropyl, t-butyl, cyclohexyl, phenyl, 4-methoxyphenyl, 4-fluorophenyl, pyridyl, —$NH_2$, methylamino, dimethylamino, benzylamino, piperidino, morpholino, piperazino, or N-methylpiperazino.

6. A compound as claimed in claim 1 wherein A and B taken together represent a bond, and $R_4$ is —$NH_2$, acetylamino, methylamino, dimethylamino, benzylamino, morpholinyl, piperidino, morpholino, piperazino or N-methylpiperazino, (methoxycarbonyl)-methylamino, (methoxycarbonyl)-phenethylamino, —OH, methoxy, allyloxy, benzyloxy.

7. A compound as claimed in claim 1 wherein A represents hydrogen and B and $R_4$ each independently represents a hydroxy group.

8. A pharmaceutical composition containing a compound as claimed in claim 1 and a pharmaceutically acceptable carrier.

9. A method of treatment of an animal suffering from a disease mediated by cysteine protease activity, which method comprises administering to the animal a sufficient amount of a compound as claimed in claim 1 to inhibit such activity.

10. A method as claimed in claim 9 wherein the disease is muscular dystrophy, osteoporosis, tumour metastasis, rheumatoid arthritis, neuronal or cardiac ischaemia, allergic immune response, or protozoal or bacterial disease.

11. A compound as claimed in claim 1 selected from the group consisting of:

2-(2S-2-benzyloxycarbonylamino-2-isopropylmethyl-acetamido)-3-amino-acrylamide;

2-(2S-2-benzyloxycarbonylamino-2-cyclohexylmethyl-acetamido)-3-amino-acrylamide;

2-(2S-2-benzyloxycarbonylamino-2-benzyl-acetamido)-3-amino-acrylamide;

2-[2S-2-(3-phenylpropionoyl)amino-2-benzyl-acetamido]-3-amino-acrylamide;

2-(2S-2-benzyloxycarbonylamino-2-isopropylmethyl-acetamido)-3-benzylamino-acrylamide;

2-(2S-2-benzyloxycarbonylamino-2-isopropylmethyl-acetamido)-3-(morpholin-4-yl)-acrylamide;

2-(2S-2-benzyloxycarbonylamino-2-isopropylmethyl-acetamido)-3-(2-hydroxyethylamino)-acrylamide;

2-(2S-2-benzyloxycarbonylamino-2-isopropylmethyl-acetamido)-3-phenylamino-acrylamide;

2-(2S-2-benzyloxycarbonylamino-2-isopropylmethyl-acetamido)-3-piperidino-acrylamide;

(2E)-(2S-2-benzyloxycarbonylamino-2-isopropylmethyl-acetamido)-3-acetamido-acrylamide;

(2Z)-(2S-2-benzyloxycarbonylamino-2-isopropylmethyl-acetamido)-3-acetamido-acrylamide;

2-(2S-2-benzyloxycarbonylamino-2-isopropylmethyl-acetamido)-3,3-dihydroxy-propionamide;

2-(2S-2-benzyloxycarbonylamino-2-cyclohexylmethyl-acetamido)-3,3-dihydroxy-propionamide;

2-(2S-2-benzyloxycarbonylamino-2-benzyl-acetamido)-3,3-dihydroxy-propionamide;

2-[2S-2-(3-phenylpropionoylamino)-2-benzyl-acetamido]-3,3-dihydroxy-propionamide;

2-(2S-2-benzyloxycarbonylamino-2-isopropylmethyl-acetamido)-3-hydroxy-acrylamide;

2-(2S-2-benzyloxycarbonylamino-2-isopropylmethyl-acetamido)-3-benzylamino-N-benzyl-acrylamide;

2-(2S-2-benzyloxycarbonylamino-2-isopropylmethyl-acetamido)-3-(4-methylpiperazino)-acrylamide;

2-(2S-2-benzyloxycarbonylamino-2-isopropylmethyl-acetamido)-3-(3-tert-butoxycarbonylamino-pyrrolidino)-acrylamide;

(2E)-(2S-2-benzyloxycarbonylamino-2-cyclohexymethyl-acetamido)-3-acetamido-acrylamide;

(2Z)-(2S-2-benzyloxycarbonylamino-2-cyclohexymethyl-acetamido)-3-acetamido-acrylamide;

tert-Butyl-2-[2S-(benzyloxycarbonylamino)-2-isopropylmethyl-acetamido]-2-(morpholino-1-methylenyl)-acetate;

Ethyl-2-[2S-(benzyloxycarbonylamino)-2-isopropylmethyl-acetamido]-2-(4-methylpiperazino-1-methylenyl)-acetate;

Ethyl-2-[2S-(benzyloxycarbonylamino)-2-phenylmethyl-acetamido]-2-(morpholino-1-methylenyl)-acetate;

Ethyl-2-[2S-(benzyloxycarbonylamino)-2-isopropylmethyl-acetamido]-2-(morpholino-1-methylenyl)-acetate;

Ethyl-2-[2S-(benzyloxycarbonylamino)-2-cyclohexylmethyl-acetamido]-2-(morpholino-1-methylenyl)-acetate;

Diphenylmethyl-2-[2S-(3-phenylpropionylamino)-2-phenylmethyl-acetamido]-2-(morpholino-1-methylenyl)-acetate;

2-[2S-(Benzothiophen-2-carbonylamino)-2-isopropylmethyl-acetamido]-2-(morpholino-1-methylenyl)-4'-methoxyacetophenone;

2-[2S-(benzyloxycarbonylamino)-2-isopropylmethyl-acetamido]-2-(morpholino-1-methylenyl)-acetophenone;

2-[2S-(benzyloxycarbonylamino)-2-isopropylmethyl-acetamido]-2-(morpholino-1-methylenyl)-4'-methoxyacetophenone;

2-[2S-(benzyloxycarbonylamino)-2-isopropylmethyl-acetamido]-2-(morpholino-1-methylenyl)-4'-fluoroacetophenone;

(2E)-(2S-2-benzyloxycarbonylamino-2-phenylmethyl-acetamido)-3-(1-carbomethoxy-2-phenethylamino)-acrylamide;

(2Z)-(2S-2-benzyloxycarbonylamino-2-phenylmethyl-acetamido)-3-(1-carbomethoxy-2-phenethylamino)-acrylamide;

(2E)-(2S-2-benzyloxycarbonylamino-2-phenylmethyl-acetamido)-3-(1-carbomethoxy-methylamino)-acrylamide; and (2Z)-(2S-2-benzyloxycarbonylamino-2-phenylmethyl-acetamido)-3-(1-carbomethoxy-methylamino)-acrylamide.

\* \* \* \* \*